United States Patent [19]

Schweden et al.

[11] Patent Number: 5,741,674
[45] Date of Patent: Apr. 21, 1998

[54] RECOMBINANT PRODUCTION OF PROTEINS IN YEAST

[75] Inventors: Jürgen Schweden, Neustadt; Claus Bollschweiler, Heidelberg; Michael Piontek, Essen; Ulrike Weydemann, Köln; Zbigniew A. Janowicz, Erkrath; Alexander W.M. Strasser, Düsseldorf, all of Germany

[73] Assignee: Rhein Biotech Gesellschaft fur neue biotechnologische Prozesse und Produkte, mbH, Duesseldorf, Germany

[21] Appl. No.: 605,053

[22] PCT Filed: Sep. 1, 1994

[86] PCT No.: PCT/EP94/02897

§ 371 Date: Mar. 1, 1996

§ 102(e) Date: Mar. 1, 1996

[87] PCT Pub. No.: WO95/07356

PCT Pub. Date: Mar. 16, 1995

[30] Foreign Application Priority Data

Sep. 4, 1993 [DE] Germany ............. 43 29 969.5

[51] Int. Cl.⁶ ......................................... C12P 21/00
[52] U.S. Cl. ............... 435/69.1; 435/254.2; 435/71.1; 435/69.7; 435/254.11; 536/23.1; 530/350
[58] Field of Search ............... 435/69.1, 254.2, 435/71.1, 69.7, 254.11; 536/23.1; 530/350

[56] References Cited

FOREIGN PATENT DOCUMENTS 173 378  3/1986  European Pat. Off. .

WO 92/13951  8/1992  WIPO .

OTHER PUBLICATIONS

Winther et al. (1991) Proc. Natl. Acad. Sci. USA, vol. 88, pp. 9330–9334, 1991.
Hiramatsu et al. (1991) Applied Environmental Microbiology, vol. 57, pp. 2052–2056, 1991.
Sudbery et al. (1988) Biochemical Society Transactions, vol. 16, pp. 1081–1083, 1988.
Chem. Abst., vol. 116, 1992 –116: 10032 p. 174.
Biotech., vol. 9, Mar. 1991, Heterologous Gene Expression ... 291–295.
Agric. Bio. Chem., 53 (2), 483–489, 1989, Threonine–and Serine–rich Tract of the ...
Biotech Dav., vol. 10, 179–189, 1992, 179–189.

Primary Examiner—Robert A. Wax
Assistant Examiner—Enrique D. Longton
Attorney, Agent, or Firm—Keil & Weinkauf

[57] ABSTRACT

A process for the recombinant production of proteins in the yeast Hansenula comprises transforming Hansenula with an expression cassette which comprises the following structural elements encoded:

L-A-P-GEN where
  L is a leader sequence,
  A is an adaptor producing an alpha-helix structure,
  P is a processing signal and
  GEN is a structural gene for the required protein.

3 Claims, 4 Drawing Sheets

SEQ ID NO: 2

```
    ggggggggaattcatgattttctgaagctg
  1 --------+---------+---------+  30
    ccccccccttaagtactaaaagacttcgac
```

```
a     G  G  E  F  M  I  F  L  K  L
b      G  G  N  S  *  F  F  F  *  S  *
c       G  G  I  H  D  F  S  E  A  D
```

```
    attaaaagtatagtaattggtttgggatta
 31 --------+---------+---------+  60
    taattttcatatcattaaccaaaccctaat
```

```
      I  K  S  I  V  I  G  L  G  L   -
       L  *  K  V  *  *  L  V  W  D  *  :
        *  K  Y  S  N  W  F  G  I  S   -
```

```
    gttagtgctatccaagcagccccctgcctct
 61 --------+---------+---------+  90
    caatcacgataggttcgtcggggacggaga
```

```
a     V  S  A  I  Q  A  A  P  A  S
b      L  V  L  S  K  Q  P  L  P  L
c       *  C  Y  P  S  S  P  C  L  F
```

```
    tcgattggatctagtgcttcagcatctagt
 91 --------+---------+---------+ 120
    agctaacctagatcacgaagtcgtagatca
```

```
                    tcaagtgagagttctcaggctacaattccc
    1 2 1 ---------+---------+---------+ 1 5 0
                    agttcactctcaagagtccgatgttaaggg a      S   S   E   S   S   Q   A   T   I   P
    b        Q   V   R   V   L   R   L   Q   F   P
    c          K   *   E   F   S   G   Y   N   S   Q aatgatgtaacattaggtgttaaacaaatt
    1 5 1 ---------+---------+---------+ 1 8 0
                    ttactacattgtaatccacaatttgtttaa N   D   V   T   L   G   V   K   Q   I      -
             M   M   *   H   *   V   L   N   K   F    -
               *   C   N   I   R   C   *   T   N   S  - cctaatatctttaatgactctgctgtcgat
    1 8 1 ---------+---------+---------+ 2 1 0
                    ggattatagaaattactgagacgacagcta
                                        SEQ ID NO: 3
    a      P   N   I   F   N   D   S   A   V   D
    b        L   I   S   L   M   T   L   L   S   M
    c          *   Y   L   *   *   L   C   C   R   C SEQ ID NO: 4
                    gctaatgcagctgctaaacaccctctggaa
    2 1 1 ---------+---------+---------+ 2 4 0
                    cgattacgtcgacgatttgtgggagacctt A   N   A   A   A   K   H   P   L   E      -
             L   M   Q   L   L   N   T   L   W   K    -
               *   C   S   C   *   T   P   S   G   K  -

FIG. 2
```

```
        aaaagagttgtttacactgactgcactgaa
241 ---------+---------+---------+270
        ttttctcaacaaatgtgactgacgtgactt
```

```
a   K  R  V  V  Y  T  D  C  T  E
b    K  E  L  F  T  L  T  A  L  N
c    K  S  S  L  H  *  L  H  *  I
```

```
        tccggtcagaacctgtgcctgtgcgaaggc
271 ---------+---------+---------+300
        aggccagtcttggacacggacacgcttccg
```

```
    S  G  Q  N  L  C  L  C  E  G   -
     P  V  R  T  C  A  C  A  K  A  -
      R  S  E  P  V  P  V  R  K  L  -
```

```
        tctaacgtttgcggccagggcaacaaatgc
301 ---------+---------+---------+330
        agattgcaaacgccggtcccgttgtttacg
```

```
a   S  N  V  C  G  Q  G  N  K  C
b    L  T  F  A  A  R  A  T  N  A
c     *  R  L  R  P  G  Q  Q  M  H
```

```
        atcctgggctctaaaggcgaacgtaaccag
331 ---------+---------+---------+360
        taggacccgagatttccgcttgcattggtc
```

```
          tgcgttactggcgaaggtaccccgcgtccg
3 6 1 ---------+---------+---------+ 3 9 0
          acgcaatgaccgcttccatggggcgaggc
```

```
a    C  V  T  G  E  G  T  P  R  P
b     A  L  L  A  K  V  P  R  V  R
c      R  Y  W  R  R  Y  P  A  S  A
```

```
          cagtctcacaacgacggcgacttcgaagaa
3 9 1 ---------+---------+---------+ 4 2 0
          gtcagagtgttgctgccgctgaagcttctt
```

```
     Q  S  H  N  D  G  D  F  E  E  -
      S  L  T  T  T  A  T  S  K  K  -
       V  S  Q  R  R  R  L  R  R  N  -
```

```
          atcccggaagaatacctgcagtaatagaga
4 2 1 ---------+---------+---------+ 4 5 0
          tagggccttcttatggacgtcattatctct
```

SEQ ID NO: 5
```
a    I  P  E  E  Y  L  Q  *  *  R
b     S  R  K  N  T  C  S  N  R  D
c      P  G  R  I  P  A  V  I  E  I
```

```
          tctagggtcgaccccccc
4 5 1 ---------+-------- 4 6 8
          agatcccagctggggggg
```

RECOMBINANT PRODUCTION OF PROTEINS IN YEAST

The present invention relates to a process for the recombinant production of proteins in the yeast Hansenula.

The recombinant production of proteins in the yeast Hansenula is known. European Patent 173378 describes the recombinant preparation of proteins using particular promoter elements of MOX or DAS. However, this document provides no information as to how efficient secretion and correct processing of the required protein is to be achieved.

Furthermore, it is known that in *Hansenula polymorpha*, the glucoamylase leader sequence (GAM1) from *Schwanniomyces occidentalis* is recognized as signal sequence, and it is possible to secrete correctly processed glucoamylase (G. Gellissen et al., Bio-technology 9 (1991) 291–295). However, this signal sequence does not lead to the secretion of gene products foreign to yeasts, for example it is not possible to secrete the protein hirudin therewith.

It is an object of the present invention to provide a process for the recombinant production of proteins, in particular of proteins which are foreign to yeasts, ie. heterologous, in the yeast Hansenula, which ensures efficient secretion and correct processing for a large number of proteins.

We have found that this object is achieved by a process for the recombinant production of proteins in the yeast Hansenula, which comprises transforming Hansenula with an expression cassette which comprises the following structural elements encoded:

L-A-P-GEN where

L is a leader sequence,

A is an adaptor producing an alpha-helix structure,

P is a processing signal and

GEN is a structural gene for the required protein.

It is possible to use as leader sequence L the leader sequences of all gene products secreted in yeast, which are recognized by Hansenula. It is not a necessary requirement that the leader sequence originates from a Hansenula gene. Leader sequences of yeasts of genera other than Hansenula are also suitable, for example Saccharomyces or Schwanniomyces. A leader sequence which is very suitable for the invention is, for example, the alpha factor leader sequence from *Saccharomyces cerevisiae* (MATα).

Leader sequences which are preferably used are those of strongly expressed and secreted hydrolytic enzymes such as alpha-amylase, invertase, acid phosphatase or glucoamylase. The glucoamylase leader sequence from *Schwanniomyces occidentalis* is particularly preferably used.

Suitable sequences as adaptor A are all those which code for a polypeptide which contains an alpha-helix structure. The presence of an alpha-helix structure can be determined by the algorithm of Garnier et al. (J. Mol. Biol. 120 (1978) 97–120). It is particularly easy to determine, using commercially obtainable computer programs based on this algorithm, whether a polypeptide sequence ought to have an alpha-helix structure.

As a rule, sequences which are very suitable as adaptor are all those for which the computer program Microgenie® (Beckmann) calculates for ALPHA a larger positive value than for the three other possible structures (BETA, TURN, COIL) for a peptide sequence of at least four amino acids in the region of the processing site A-P-GEN.

The length of the adaptor sequence A can vary within wide limits for the use according to the invention. As a rule, it is from five to one hundred amino acids.

A sequence of the glucoamylase from *Schwanniomyces occidentalis* which contains amino acids 23–72 (GAM 23–72; Dohmen et al. Gene 95 (1990), 111–121) is preferably used as adaptor sequence.

This sequence can be used as adaptor sequence directly or, particularly preferably, after extension at the C terminus by one to four amino acids. Parts of this sequence, preferably those obtained by N-terminal truncation, are also very suitable for the process according to the invention.

It is also possible, for example, by means of the computer program described above, for the sequence regions which particularly contribute to the alpha-helix formation to be identified and also optimized in respect of the alpha-helix structure by exchange of individual amino acids.

A sequence which has proven particularly suitable as adaptor for the preparation of thrombin inhibitors, especially hirudin and hirudin derivatives, by the process according to the invention is the following:

GAM 23–72-His-Pro-Leu-Glu    (SEQ ID NO: 1)

If this sequence (=A) is combined with the leader sequence of glucoamylase (GAM 1–22) (=L) the result is a leader-adaptor sequence with the structure GAM 1–72-His-Pro-Leu-Glu comprising 76 amino acids, which is particularly advantageous for the process according to the invention.

The processing signal P serves to cleave the propeptide to the mature form. Normally, a sequence of basic amino acids is used as processing signal. A very suitable processing signal is the KEX2 recognition site from *S. cerevisiae*, which consists of the dipeptide Lys-Arg and is also recognized by the yeast Hansenula. This dipeptide can also be used in duplicated form as processing signal. The sequence Lys-Arg is preferred as P.

Heterologous and homologous genes can be used as structural gene GEN for the protein to be produced. The genes can be isolated from the appropriate organisms or prepared by synthesis. In the case of chemical gene synthesis it is also possible, if required, to adapt the codon usage to the producer organism.

Eukaryotic genes are preferably employed as structural genes. The process according to the invention succeeds particularly well for the production of thrombin inhibitors, for example hirudin. This process is also very suitable for the production of human polypeptides, for example peptide hormones, growth factors and lymphokines.

The abovementioned structural elements are arranged in a known manner in the sequence L-A-P-GEN in an expression cassette. The linkage normally takes place by ligation of compatible restriction fragments or by chemical synthesis.

The expression cassettes may furthermore contain a number of conventional regulation signals such as promoters, ribosome binding sites and terminators, which are functionally connected to the structural elements L-A-P-GEN according to the invention.

The expression cassette can be part of an autonomously replicating or else an integrative vector. The construction of an expression vector using the expression cassette is described in Example 1.

The yeast Hansenula is transformed with the appropriate expression vector which contains the expression cassette. This can take place, for example, by the protocol described in Example 2.

Stably expressing clones which are suitable as producer organism in the process according to the invention are isolated from the yeast transformed in this way. The producer organisms are cultivated under conventional conditions and produce the required protein in a constitutive or inducible manner depending on the regulation elements selected. The protein is secreted by the producer organism into the surrounding medium, from where it can easily be isolated and purified.

Purification from the medium takes place as a rule, after the producer organism has been removed, by purification processes familiar in protein chemistry.

The process according to the invention provides correctly processed mature proteins without the faulty processing otherwise observed. This process therefore leads to a high yield of mature protein and considerably facilitates the subsequent purification steps. This process can therefore be employed particularly well for the production of drugs based on pharmaceutical proteins.

The following examples explain the invention further.

EXAMPLE 1

Construction of vectors for the secretory expression of recombinant proteins from the yeast strain *Hansenula polymorpha*

This example describes the construction of expression vectors which are used in the production according to the invention of recombinant proteins in *Hansenula polymorpha*. The expression cassette used for this purpose comprises inter alia the following constituents:

Leader: Amino acid 1–22 of the glucoamylase sequence from *Schwanniomyces occidentalis* (Dohmen et al. Gene 95 (1990), 111–121)

Adaptor: SEQ ID NO: 1

Processing signal: Lys-Arg

GEN: Thrombin inhibitor gene

Starting from the abovementioned glucoamylase sequence from *Schwanniomyces occidentalis*, the GAM sequence from base pair 1 to 207 (corresponds to amino acid 1 (Met) to amino acid 69 (Ala) Fig.) was prepared with the aid of synthetic oligonucleotides and PCR amplification.

Two oligonucleotides with the sequences SEQ ID NO: 2 and NO: 3 were prepared and used as amplification primers for the PCR.

The resulting GAM leader-adaptor part-fragment was then cut with EcoRI at the 5' end and with PvuII at the 3' end.

For the secretory preparation of hirudin, an adaptor-processing signal-hirudin gene (A-P-GEN) was prepared starting from the known hirudin gene with the aid of two synthetic oligonucleotides and PCR amplification. The oligonucleotides used for this had the sequences SEQ ID NO: 4 and SEQ ID NO: 5.

The amplified DNA fragment was then cut at the 5' end with PvuII and at the 3' end with SalI.

Ligation of the 3'-end PvuII site of the GAM-leader-adaptor part-fragment to the 5'-end PvuII site of the A-P-GEN, and ligation of this fragment via EcoRI/SalI into pUC18, completed the construct.

The L-A-P-GEN fragment was in turn isolated from this construct as EcoRI/BglII fragment and ligated into the appropriately prepared *H. polymorpha* expression vector pFMD 13025 (Gellissen G. et al., TIBTECH, 10 (1992) 413–417). This entails fusion of the 5' end of L-A-P-GEN to the *H. polymorpha* promoter and of the 3' end of the fragment to the *H. polymorpha* terminator. The expression cassette is now complete and a constituent of a shuttle vector with which both *E. coli*, for the purpose of propagation, and the yeast *H. polymorpha*, for the purpose of expression of the foreign gene, can be transformed.

The same L-A-P construction was fused to the gene for the thromobin inhibitor rhodniin from Rhodnius prolixus (WO 93/8282) and to the gene for the thrombin inhibitor moubatin from Ornithodorus moubata (WO 93/9232). The expression cassettes obtained in this way were employed in a similar way to the hirudin gene fusions for constructing *Hansenula polymorpha* expression vectors.

EXAMPLE 2

Transformation of *Hansenula polymorpha* with the expression vectors

The host strain for the transformation is an auxotrophic mutant obtained by EMS mutagenesis: a strain with a deficiency for orotidine-5'-phosphate dehydrogenase ($ura^-$). The reversion rate of this uracil mutant can be neglected.

Competent cells of this strain were obtained in the following way (method of Dohmen et al., Yeast 7 (1992) 691–692):

10 ml of yeast complete medium (YPD) were inoculated with the host strain and cultivated by shaking at 37° C. overnight. This preculture was transferred into 200 ml of YPD medium and cultivated by shaking at 37° C. until the $OD_{600\ nm}=0.6–1.0$. The cells were washed with 0.5 ml volume of solution A (1M sorbitol, 10 mM bicine pH 8.35, 3% ethylene glycol) at room temperature and subsequently resuspended in 0.02 volume of solution A.

After adding 11 µl of DMSO, the aliquots were stored at −70° C. until the transformation was carried out.

For the transformation, 10 µg of plasmid DNA and 100 µl of cold 0.1M calcium chloride solution were added directly to the frozen competent cells.

After rapid thawing at 37° C., each transformation mixture was incubated with 1.0 ml of solution B (40% polyethylene glycol PEG 3350, 200 mM bicine pH 8.35) at 37° C. for one hour. The cells were then washed in 1 ml of solution C (150 mM NaCl, 10 mM bicine pH 8.35), resuspended in 200 µl of solution C and plated onto selective medium (YNB glucose, complementation of the uracil deficiency by $ura^+$ expression plasmids). Incubation took place at 37° C. for 3–5 days.

EXAMPLE 3

Isolation of mitotically stable clones

The recombinant expression plasmids used for transforming *H. polymorpha* are autonomously replicating and can integrate spontaneously into the yeast genome. They form a multimeric structure therein: the plasmid monomers are connected together head to tail. Several copies of the expression cassette therefore contribute to production of the recombinant gene product. The productivity of a recombinant strain is linearly related to the number of integrated expression cassettes over a wide range. Multimeric integration of the foreign DNA into the yeast genome and isolation of mitotically stable clones was achieved in the following way:

The transformants were inoculated from the agar plates with selective medium into 3 ml of appropriate liquid medium and passaged, ie. repeated transfer into fresh YNB glucose medium (50 µl in 3 ml of medium, cultivations at 37° C.) over a period of 1–2 weeks. During this passaging, the plasmid DNA integrated into the yeast genome so that mitotically stable clones were then obtained.

The mitotic stability was tested in the following way:

Three transfers were made from the last passaging culture in YNB glucose medium into complete medium (YPD) and cultivated at 37° C. for 1–2 days. The diluted culture was then plated onto complete medium and onto selective medium. Mitotically stable transformants give approximately the same number of colonies on the two media. It is thus possible to isolate mitotically stable sub-transformants (Z. A. Janowicz et al., Yeast 7 (1991) 431–443).

EXAMPLE 4

Expression of foreign gene

For expression studies, the passaged transformants were inoculated into 3 ml of YNB medium containing 1% glycerol or 1% methanol in order to induce MOX or FMD promoters. The cells were cultivated at 37° C. for two days and then spun down, and the culture supernatant was tested for foreign protein (Western blot, ELISA, activity assay).

50 ml of synthetic medium containing 1.5% glycerol in a 500 ml Erlenmeyer flask with baffles were inoculated with efficiently secreting mitotically stable transformants and incubated to $OD_{600\ nm}=10$. HPLC analyses of corresponding culture supernatants showed that the hirudin variant is completely correctly processed on use of the sequence GAM 1–72-His-Pro-Leu-Glu as leader-adaptor.

EXAMPLE 5

Fermentation of recombinant yeast strains

The recombinant yeast strains were fermented in synthetic media (double-concentrated YNB medium 2.8 g/l (Difco) containing 10 g/l ammonium sulfate) which had been either introduced completely at the start of the fermentation or were fed in during the fermentation.

The carbon sources employed were glycerol and methanol or mixtures of glycerol and methanol. The fermentation was started with glycerol as the sole carbon source ($\geq 1\%$ glycerol final concentration in the fermenter during the initial growth phase).

After sterilization of the medium, it was inoculated with 1 l of preculture so that the initial $OD_{600\ nm}$ was about 1.

The fermentation took place in two phases: an initial growth phase with a higher glycerol concentration (1%) was followed by a production phase with a lower glycerol concentration (<0.5%) or constant methanol concentration (1%) or a mixture of glycerol and methanol (0.1–0.4% glycerol and 0.2–1.0% methanol).

The carbon source was fed in where appropriate with various control possibilities (continuously or $pO_2$-coupled).

During the fermentation there was addition of ammonium sulfate to a final concentration of 5 g/l, thiamine to a final concentration of 0.1 g/l and biotin to a final concentration of 0.3 mg/l.

The pH of the fermentation was kept constant at 4.0 by adding aqueous ammonia; the fermentation temperature was 37° C.

The recombinant yeast strains fermented in this way provided a gene product (hirudin) which was 100% correctly processed.

BRIEF DESCRIPTION OF THE FIGURE

FIG. 1: Nucleic acid sequence of the GAM-leader-adaptor-processing signal-hirudin gene fragment and of the polypeptide sequence encoded thereby (reading frame a). The position of the PCR primers is indicated.

---

We claim:

1. A process for the recombinant production of proteins which are heterologous in the yeast Hansenula, which comprises transforming Hansenula with an expression cassette which comprises the following structural elements encoded:

L-A-P-GEN where

L is a leader sequence,

A is an adaptor with the sequence SEQ ID NO:1,

P is a processing signal and

GEN is a structural gene for the required protein;

growing Hansenula in a suitable growth medium;

and recovering said protein; wherein said protein is correctly processed.

2. A process as defined in claim 1, wherein the leader sequence of the glucoamylase from *Schwanniomyces occidentalis* is used as leader sequence L.

3. A process as defined in claim 1, wherein the peptide sequence Lys-Arg is used one or more times as processing signal P.

* * * * *

UNITED STATES PATENT AND TRADEMARK OFFICE
CERTIFICATE OF CORRECTION

PATENT NO. : 5,741,674
DATED : April 21, 1998
INVENTOR(S) : SCHWEDEN et al.

It is certified that error appears in the above-identified patent and that said Letters Patent is hereby corrected as shown below:

On the cover page, item [73] should read:

--BASF Aktiengesellschaft, Ludwigshafen, Germany and Rhein Biotech Gesellschaft für neue biotechnologische Prozesse und Produkte mbH, Duesseldorf, Germany--.

Signed and Sealed this

Third Day of August, 1999

Q. TODD DICKINSON

*Attest:*

*Attesting Officer*  Acting Commissioner of Patents and Trademarks

SEQUENCE LISTING ( 1 ) GENERAL INFORMATION:

( i i i ) NUMBER OF SEQUENCES: 5

( 2 ) INFORMATION FOR SEQ ID NO: 1:

( i ) SEQUENCE CHARACTERISTICS:
( A ) LENGTH: 54 amino acids
( B ) TYPE: amino acid
( C ) TOPOLOGY: linear ( i i ) MOLECULE TYPE: peptide ( v ) FRAGMENT TYPE: internal ( v i ) ORIGINAL SOURCE: Schwanniomyces occidentalis ( x i ) SEQUENCE DESCRIPTION: SEQ ID NO: 1:

```
Ala Pro Ala Ser Ser Ile Gly Ser Ser Ala Ser Ala Ser Ser Ser Ser
 1               5                  10                  15
Glu Ser Ser Gln Ala Thr Ile Pro Asn Asp Val Thr Leu Gly Val Lys
                20                  25                  30
Gln Ile Pro Asn Ile Phe Asn Asp Ser Ala Val Asp Ala Asn Ala Ala
                35                  40                  45
Ala Lys His Pro Leu Glu
        50
```

( 2 ) INFORMATION FOR SEQ ID NO: 2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 2:

GGGGGGGAAT TCATGATTTT TCTGAAGCTG ATT        33

( 2 ) INFORMATION FOR SEQ ID NO: 3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 3:

GGGGGGCAGC TGCATTAGCA TCGACAGCAG A        31

( 2 ) INFORMATION FOR SEQ ID NO: 4:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 4:

GGGGGGCAGC TGCTAAACAC CCTCTGGAAA AAAGAGTTGT TTACACTGAC TGCACT        56

( 2 ) INFORMATION FOR SEQ ID NO: 5:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: genomic DNA ( x i ) SEQUENCE DESCRIPTION: SEQ ID NO: 5:

GGGGGGGTCG ACCCTAGATC TCTATTACTG CAGGTATTCT TCCGG        45